United States Patent [19]

Bauman

[11] 3,961,074

[45] June 1, 1976

[54] KETO-QUATERNARY COMPOSITIONS

[75] Inventor: Robert Andrew Bauman, New Brunswick, N.J.

[73] Assignee: Colgate-Palmolive Company, New York, N.Y.

[22] Filed: May 9, 1975

[21] Appl. No.: 576,082

Related U.S. Application Data

[60] Division of Ser. No. 445,542, Feb. 25, 1974, Pat. No. 3,907,895, which is a continuation-in-part of Ser. No. 400,097, Sept. 24, 1973, which is a continuation of Ser. No. 39,536, May 21, 1970, abandoned.

[52] U.S. Cl. .................................. 424/54; 424/329
[51] Int. Cl.² ........................................... A61K 7/22
[58] Field of Search .............................. 424/329, 54

[56] References Cited
UNITED STATES PATENTS
3,565,942   2/1971   Kvimmel ........................... 260/468

*Primary Examiner*—Jerome D. Goldberg
*Attorney, Agent, or Firm*—Robert L. Stone; Murray M. Grill; Herbert S. Sylvester

[57] ABSTRACT

Novel keto-quaternary ammonium compounds which include the adamantane ring system linked to the quaternary ammonium group by a keto group.

6 Claims, No Drawings

KETO-QUATERNARY COMPOSITIONS

This is a divisional of application Ser. No. 445,542 filed Feb. 25, 1974, now U.S. Pat. No. 3,907,895 issued Sept. 23, 1975 which is a continuation-in-part of copending application Ser. No. 400,097 filed Sept. 24, 1973, which is a continuation of patent application 39,536 filed May 21, 1970, now abandoned.

The present invention relates to novel quaternary ammonium compounds represented by the general formula:

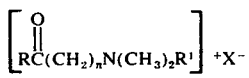

wherein R is 1-adamantyl ($C_{10}H_{15}$), $R^1$ is a long chain alkyl group of 10–18 carbon atoms, n is an integer from 1 to 3 and X is a compatible anion such as the halides ($Cl^-$, $Br^-$, $I^{--}$), sulfates (i.e., methyl sulfate), nitrates, aryl sulfonates, etc. These quaternary compounds possess superior anti-microbial, anti-caries and anti-calculus activity.

The adamantyl radical is derived from tricyclo-[3.3.1.1$^{3,7}$]decane showing four fused chair cyclohexane rings as follows:

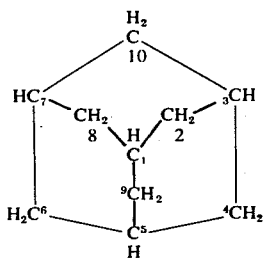

Typical examples of the quaternary ammonium compounds which may be used in this invention are:
2-adamantylcarbonylethyldimethyldecylammonium-bromide,
3-adamantylcarbonylpropyldimethyltetradecyl ammonium bromide,
2-adamantylcarbonylethyldimethylhexadecylammonium bromide,
1-adamantylcarbonylethyldimethyloctadecylammonium bromide,
1-adamantylcarbonylmethyldimethyltetradecylammonium bromide,
1-adamantylcarbonylmethyldimethyldodecylammonium bromide.

Other halides such as the chlorides, iodides and analogous compounds such as the sulfates, nitrates, aryl sulfonates, etc., may also be employed herein as effective anti-bactericides.

It has been observed that the compounds generally described by the foregoing formula are particularly effective against gram positive organisms such as *Staphylococcus aureus*, *Streptococcus mitis*, *Bacillus subtilis*, *Corynebacterium acnes*, and against fungi, such as *Candida albicans*, *Trichophyton mentogrophytes* and *Aspergillus niger*, and moderately effective against *Escherichia coli* which is a gram negative bacterium. Compounds wherein $R^1$ is a benzyl radical in lieu of instant higher alkyl radical would be devoid of antibacterial activity.

The anti-microbial nature of the instant novel compounds was shown by a standard test tube serial dilution test in which an appropriate number of test tubes of broth containing decreasing concentrations of the test agent was inoculated with the test organism. After a suitable period of incubation the tubes were examined for the presence or absence of growth. The activity of the test agent was the lowest concentration which inhibited the growth of the organism and is expressed as the minimal inhibitory concentration in ug/ml.

In general, smaller concentrations of the subject compounds are required to inhibit the growth of the organisms than of analogous compounds which contain substantially the same number of carbon atoms.

When used against bacteria or fungi, compounds of the instant invention may be applied directly to the surface to be protected or may be dissolved in a pharmaceutical carrier. Typically, an effective amount, e.g. 0.1 to about 10% by weight of the compound, is included in an inert carrier and a dispersing or surface active agent. Alternatively, an effective amount, e.g. 0.1 to about 10% by weight may be incorporated into a solid carrier which may be inert, such as talc, clay, diatomaceous earth, flour, etc.

When compounds of the instant invention are intended for use in compositions which reduce formation of caries and inhibit formation of oral calculus, they are typically incorporated in oral preparations in effective amounts up to about 5% by weight, preferably .025–1% and most preferably 0.05–0.5% by weight of the oral preparation. Typically, the oral preparation is a dentrifrice, such as a dental cream, tablet or powder, containing as a vehicle about 20–95% by weight of a water-insoluble polishing material, preferably including water-insoluble phosphate such as dicalcium, phosphate, tricalcium phosphate, trimagnesium phosphate. The dentrifrice may also include water; binders such as glycerine, sorbitol, propylene glycol, and polyethylene glycol 400; detergents; gelling agents such as Irish moss and sodium carboxymethyl cellulose; additional antibacterial agents; coloring or whitening agents; preservatives; silicones; chlorophyll compounds; additional ammoniated materials; flavoring or sweetening materials; and compounds which provide fluorine-containing ion such as sodium fluoride, stannous fluoride and sodium monofluorophosphate.

The oral preparation may also be a liquid such as mouth rinse which typically contains 20–99% by weight of an aqueous lower aliphatic alcohol, preperably having about 1–30% by weight alcohol, such as ethanol, n-propyl, or isopropyl alcohol.

Such oral preparations are typically applied by brushing the teeth or rinsing the oral cavity for 30–90 seconds at least once daily. Typical oral preparations of the invention which can be applied in this manner are set forth below.

EXAMPLE 1
Dental Cream

|  | % |
|---|---|
| Quaternary ammonium adamantylketone | 0.50 |
| *Nonionic detergent | 1.00 |
| Glycerine | 22.00 |
| Sodium pyrophosphate | 0.25 |
| Carboxymethyl cellulose | 0.85 |
| Sodium saccharin | 0.20 |
| Sodium benzoate | 0.50 |
| Calcium carbonate (precipitated) | 5.00 |

-continued

| | |
|---|---|
| Dicalcium phosphate dihydrate | 46.75 |
| Flavor | 0.80 |
| Water | 22.15 |

*Tween 80 - Polyoxyethylene (20 moles ethylene oxide) sorbitan monooleate

EXAMPLE 2
Mouth Wash

| | % |
|---|---|
| Quaternary ammonium adamantylketone | 0.05 |
| *Nonionic detergent (Pluronic F-68) | 1.00 |
| Ethyl alcohol (containing flavor) | 15.00 |
| Glycerine | 10.00 |
| Saccharin | 0.02 |
| Water | 73.93 |

*Block polymer of 80% polyoxyethylene and 20% polyoxypropylene

The quaternary ammonium adamantyl ketones can be prepared by a two step process of reacting a compound containing the adamantane radical with a compound containing the dimethylamine radical, followed by quaternizing with a higher aliphatic halide. Another method of preparing instant adamantyl ketones comprises reacting adamantylhalo - lower alkyl ketone with dimethyl higher alkyl amine.

The following examples illustrate the manner in which compounds of this invention are prepared.

EXAMPLE 3

Preparation of 1-adamantylcarbonylmethyldimethyltetradecylammonium bromide.

A mixture of 1.3g. (0.005 mole) 1-adamantyl bromomethyl ketone and 1.23g. (0.005 mole) dimethyltetradecylamine was solubilized by the addition of 30cc acetone. The next day the solidified mixture was washed with ether and recrystallized from ethyl acetate to yield 2.1g. white crystals, m.p. 134°–135.5°C.

| | Found | Calculated |
|---|---|---|
| Carbon | 67.72 | 67.45 |
| Hydrogen | 10.65 | 10.51 |

EXAMPLE 4

The dodecyl homolog was prepared by the procedure of Example 3 yielding white crystals of melting point 140°–141.5°C and with the following analysis.

| | Found | Calculated |
|---|---|---|
| Carbon | 66.55 | 66.36 |
| Hydrogen | 9.87 | 10.28 |

Although this invention has been described with reference to specific examples, it will be apparent to one skilled in the art that various modifications may be made thereto which fall within its scope.

What is claimed is:

1. A pharmaceutical composition comprising about 0.1–10% by weight of a chemical compound having the structural formula:

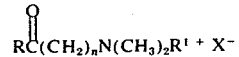

wherein R is 1-adamantyl, $R^1$ is a long chain alkyl group of 10 to 18 carbon atoms, n is an integer from 1 to 3, and X is a compatible anion selected from the group consisting of chloride, bromide, iodide, methyl sulfate, nitrite and arylsulfonates.

2. A pharmaceutical composition as set forth in claim 1, wherein X is a halide.

3. An oral preparation comprising an effective amount to reduce caries formation and inhibit calculus formation up to about 5% by weight of a chemical compound having the structural formula:

wherein R is 1-adamantyl, $R^1$ is a long chaim alkyl group of 10 to 18 carbon atoms, n is an integer from 1 to 3, and X is a compatible anion admixed with an oral vehicle selected from the group consisting of chloride, bromide, iodide, methyl sulfate, nitrate and arylsulfonates.

4. An oral preparation as set forth in claim 3 wherein said compound is 1-adamantanecarbonylmethyldimethyldodecyl ammonium bromide.

5. An oral preparation as set forth in claim 3 wherein said compound is 1-adamantanecarbonylmethyldimethyltetradecyl ammonium bromide.

6. An oral preparation as set forth in claim 3 wherein said compound is present in amount of about 0.025–1% by weight.

* * * * *